(12) United States Patent
Kariyama et al.

(10) Patent No.: US 8,663,556 B2
(45) Date of Patent: Mar. 4, 2014

(54) METHOD FOR STERILIZING POWDER OR GRAIN AND STERILIZING APPARATUS EMPLOYING THE SAME

(75) Inventors: Masahiro Kariyama, Okayama (JP); Toshio Hirata, Okayama (JP); Fumihiro Sato, Okayama (JP); Akira Mori, Okayama (JP); Hidehi Takebe, Yokohama (JP)

(73) Assignee: Fujiwara Techno-Art Co., Ltd., Okayama (JP)

( * ) Notice: Subject to any disclaimer, the term of this patent is extended or adjusted under 35 U.S.C. 154(b) by 336 days.

(21) Appl. No.: 12/994,128

(22) PCT Filed: May 26, 2009

(86) PCT No.: PCT/JP2009/059623
§ 371 (c)(1),
(2), (4) Date: Nov. 22, 2010

(87) PCT Pub. No.: WO2009/145198
PCT Pub. Date: Dec. 3, 2009

(65) Prior Publication Data
US 2011/0104006 A1    May 5, 2011

(30) Foreign Application Priority Data
May 26, 2008   (JP) ................................. 2008-137315

(51) Int. Cl.
*A61L 2/00* (2006.01)
*A61L 2/04* (2006.01)
*A61L 9/00* (2006.01)
*A61L 11/00* (2006.01)
*C23F 11/00* (2006.01)

(52) U.S. Cl.
USPC ............................................... 422/39; 422/1

(58) Field of Classification Search
USPC ....................................... 422/39, 1
See application file for complete search history.

(56) References Cited

U.S. PATENT DOCUMENTS

| 4,059,919 | A  | * | 11/1977 | Green ................................. 47/1.1 |
| 4,709,487 | A  |   | 12/1987 | Akao et al. |
| 2003/0194347 | A1 | * | 10/2003 | He et al. ........................... 422/29 |
| 2012/0122192 | A1 | * | 5/2012 | Trimbur et al. ............. 435/257.2 |

FOREIGN PATENT DOCUMENTS

EP    0061305 A    9/1982
(Continued)

OTHER PUBLICATIONS

English translation of JP 2000-024091, Jan. 25, 2000.*

*Primary Examiner* — Regina M Yoo
(74) *Attorney, Agent, or Firm* — DLA Piper LLP (US)

(57) ABSTRACT

[Problem to be solved] To provide a method for sterilizing powder or grain by which the heating time is a minimum required time to reduce thermal degradation of the quality of the powder or grain while securing sufficient sterilization effect, and a sterilizing apparatus employing the method.
[Means to solve the problem]
The problem is solved by a method for sterilizing powder or grain, and a sterilizing apparatus employing the method, and the method includes applying heat and pressure in which powder or grain is supplied into a heated gas flow pipe kept under heated and pressurized conditions, and the powder or grain is transferred while coming into direct contact with a heated condensable gas in the heated gas flow pipe for 0.008 to 2 seconds, and instantaneous reduced pressure sterilizing in which the heated condensable gas and the powder or grain are instantaneously released into a space having a pressure lower than that in the heated gas flow pipe, water contained in microorganisms adhering to the powder or grain is boiled rapidly, and tissues of the microorganisms are destroyed.

4 Claims, 2 Drawing Sheets

(56) References Cited

FOREIGN PATENT DOCUMENTS

| | | |
|---|---|---|
| JP | H05-53 B | 1/1993 |
| JP | H07-114674 B | 12/1995 |
| JP | 2000-24091 A | 1/2000 |
| JP | 2000-157615 A | 6/2000 |
| WO | WO 2004/049825 A | 6/2004 |

* cited by examiner

METHOD FOR STERILIZING POWDER OR GRAIN AND STERILIZING APPARATUS EMPLOYING THE SAME

TECHNICAL FIELD

The present invention relates to a method for sterilizing powder or grain that can destroy microorganisms from the inside by heating and rapid pressure reduction, that can minimize the quality degradation of a sterilized material, and that can provide sufficient sterilization, and to a sterilizing apparatus employing the method. Furthermore, the method for sterilizing powder or grain and the sterilizing apparatus employing the method of the present invention can be applied to kill insect pests and their eggs.

BACKGROUND ART

The surface of powder or grain such as flour, rice flour, spices such as pepper, tea powder, chlorella powder or grain, and cosmetic powder is contaminated with microorganisms such as airborne bacteria and fungi. Proliferation of the microorganisms degrades the quality of the powder or grain with time. When conditions are suitable for the proliferation of the microorganisms, for example, high temperatures and humidity, especially during the transportation or processing of the powder or grain, the microorganisms may proliferate explosively to cause great damage.

Furthermore, powder or grain may be contaminated with insect pests such as maize weevil and Indian meal moth or with their eggs to cause the quality degradation of the powder or grain.

Various sterilization methods have been studied for preventing the proliferation of such harmful organisms as microorganisms and insect pests and been put into practical use. For example, as for the sterilization of microorganisms, powder or grain commonly undergoes sterilization methods in which the powder or grain is sterilized (thermally sterilized) by indirect or direct heating with Joule heating, induction heating, heated air, hot water, steam, superheated steam, or pressurized steam.

In order to sterilize microorganisms by heating, microorganisms are exposed to heating at a predetermined temperature for a predetermined period for sterilization. A large wealth of knowledge has been accumulated about the relation between the predetermined temperature and the predetermined period for heat exposure. Thermal sterilization is widely used in the food industry because thermal sterilization is a highly safe method for sterilizing food and has been proven in various sterilization applications to accumulate the knowledge and data for securing a predetermined sterilization level.

For example, Patent. Document 1 discloses in paragraph [0009] an apparatus that includes a raw material supplying unit (reference numerals 2 to 8 in FIG. 1) in which powder or grain is supplied with pressure with air that is heated and pressurized at a temperature of about 80 to 200° C. and a pressure of ambient pressure to about 10 kg/cm²G (corresponding to 0.1 to 1 MPaG) toward a first nozzle and a steam supplying unit (reference numerals 14 to 17 in FIG. 1) in which steam 13 and air 14 are mixed to be supplied to a first throttle nozzle 9. It is supposed that the powder or grain supplied from the raw material supplying unit and the mixed gas of steam and air supplied from the steam supplying unit are mixed in a heating apparatus 12 to perform thermal sterilization. It is described that the heating apparatus 12 has an outlet provided with a second throttle nozzle (paragraph [0010]).

The invention of Patent Document 1 superficially resembles an embodiment of the apparatus of the present invention. However, paragraph [0009] describes that the temperature is 80 to 200° C., the pressure is ambient pressure to 10 kg/cm²G, and the residence time is 3 to 60 seconds in the heating apparatus 12. As described in paragraph [0034], when the heating apparatus is a straight pipe, the flow rate of the mixed gas is 20 m/second, and the residence time is 0.5 to 2 seconds, the straight pipe has a large length of 10 to 40 m. Accordingly, a cyclone as shown in FIG. 8 is required to gain the residence time and to downsize the apparatus.

This is backed by the fact that, in an embodiment described in paragraph [0040] of Patent Document 1, the flow rate of the mixed gas is 15 m/second and the residence time is 4 seconds, and when a straight pipe is used, its length becomes as large as 60 m. This is supposed to be because the sterilization method of Patent Document 1 mainly depends on heating and a heat history sufficient for killing microorganisms cannot be obtained unless heating lasts for at least several seconds.

Patent Document 2 provides a heating method that includes supplying powder or grain material into a pressurized and heated medium flow such as superheated steam to mix and transfer them, transferring the transferring medium flow of the pressurized and heated medium mixed with the powder or grain material into a heated pipe generating a swirling flow provided downstream, and swirling the transferring medium along the flow in the heated pipe generating a swirling flow to spirally transfer the powder or grain material. The heated pipe generating a swirling flow is heated indirectly. As described in column 4, the method is intended to thermally sterilize and thermally denature powder or grain.

Patent Document 2 describes in column 6 that the condition of direct heating is preferably at a comparatively low temperature for sterilization, and the raw material is treated for 0.1 to 3 seconds by direct contact with saturated steam at a gauge pressure of 5 kg/cm² or less and preferably of 0.5 to 2.5 kg/cm², or with superheated steam at a gauge pressure of 4 kg/cm² or less and a temperature of 300° C. or less and preferably a pressure of 0.1 to 3 kg/cm² and a temperature of 250° C. or less. However, even the shortest treatment time among the embodiments requires 0.7 second, using superheated steam at 194° C. (Embodiment 1). In comparison with Patent Document 1, the treatment temperature is higher, but the treatment time is considerably reduced. However, there is no description whether the bacterium used in the embodiments is a heat-resistant bacterium or not. Treatment of heat-resistant bacteria may require a longer time Thus, further reduction in the treatment time and treatment temperature may reduce the quality degradation of the sterilized material.

Furthermore, Patent Document 2 describes in column 4 that pressure control provides smooth and efficient thermal denaturation, and in column 7 that, when a nozzle is used as the discharging device, pressure is reduced in a shorter period than with a rotary valve to obtain larger swelling. However, there is no description that this swelling (pressure reduction) contributes to sterilization. Thus, the method is achieved by thermal sterilization. Cited Document 2 specifically describes that provided is a heating method and a heating apparatus by which powder or grain material is efficiently thermally sterilized with a heated medium of superheated steam and by which powder or grain materials that are cereals, food, and the like are efficiently thermally denatured as well as the apparatus or system can be downsized (line 5 in column 4). Furthermore, it describes that then the raw material flowing in the pipe as a swirling flow flows along the pipe wall to be heated because the pipe is indirectly heated with the heating unit, and thus the raw material is efficiently heated, and that then the raw material is sterilized or thermally denatured because the transferring stream is pressurized, and the pressure of the stream is controlled with the downstream throttle depending on the progress of heating (line 10 in column 5). The description clearly shows that Cited Document 2 discloses sterilization involving heating.

Patent Document 3 provides a method for sterilizing powder or grain that includes aspirating powder or grain by an ejector 3 (FIG. 1) using superheated steam as a drive source, compressing and mixing the powder or grain and the superheated steam, thermally sterilizing the powder or grain, and thereafter separating the powder or grain from the superheated steam to collect, and in which both of the powder or grain and the superheated steam are aspirated into the ejector 3 using the superheated steam as the drive source. It describes in paragraph [0016] that the material and the superheated steam are aspirated, then compressed, mixed, and heated in a diffuser 19 accompanied with superheated steam that is discharged from the outlet of a nozzle 17, and that thermal conductivity in this process is large and thus the material is thermally sterilized rapidly. The description shows that Cited Document 3 also discloses sterilization by the latent heat of steam.

Each of the techniques of Patent Documents 1 to 3 is a thermal sterilization method in which microorganisms such as bacteria and fungi adhering to powder or grain raw materials are heated to raise the temperature of the whole of the powder or grain, and thus polysaccharides, proteins, lipids, nucleic acids, and the like included in the microorganisms are denatured.

However, such methods have a problem that, in order to keep the level sufficient for sterilization by such conventional heating method, powder or grain raw materials themselves are heated unnecessarily. Then, part of the starch, protein, lipid, and the like in the raw materials is denatured to change their characteristics as food raw materials and the like, and thus their commercial value is reduced. Ideally, such a short heating time that only microorganisms present on the surface of powder or grain are heated while the inside of the powder or grain remains unheated is desirable. However, because such a short heating time cannot provide a long enough heat history to kill the microorganisms, the heating time cannot be reduced.

Accordingly, in the conventional thermal sterilization methods, a sterilization condition under which the heat history of the powder or grain raw material becomes as small as possible is identified and the heating condition is controlled depending on the purpose of sterilization. In other words, even when the sterilization level is intended to be high, because heat degrades the powder or grain raw material or heating in the presence of oxygen causes rapid oxidation to significantly degrade the quality of the material, the conventional thermal sterilization methods have limitations in increasing the sterilization level.

In particular, microorganisms forming spores (heat-resistant bacteria) are covered with robust superficial tissues and thus can be killed only in an extremely stronger sterilization condition in comparison with microorganisms of normal vegetative cells. Thus, when reliable sterilization is required, the heating time must be set long.

Therefore, with respect to the heat-resistant bacteria, non-thermal sterilization by radiation exposure, ultraviolet exposure, ozone, or the like has been studied and some of them are put into practical use. In these methods, radiation rays or ultraviolet rays are applied and thus the energy of electromagnetic waves thereof destroys tissues and the like for sterilization. On the other hand, ozone has strong oxidative effect to destroy bacterium tissues for sterilization. However, these non-thermal sterilization methods have problems that they have less certainty of sterilization and a part not irradiated with the electromagnetic waves is not sterilized. In the method employing ozone, when microorganisms have a part that cannot be in contact with ozone, the part is not sterilized. Furthermore, radiation exposure has a safety concern especially when applied to food, and thus the sterilization methods are not permitted in Japan and other countries.

In contrast, examples of the method for killing insects and eggs include a method for killing insects and eggs by reduced pressure as in Patent Document 4. According to an embodiment, it is described that the method includes placing a material to be treated in a closed container under a pressure of 5 to 60 atmospheres for about 3 to 20 minutes, and rapidly or slowly reducing the pressure from the above-described condition to kill insects. The method must be a batch-wise method in order to keep the pressurized condition for several minutes, and thus has a problem of low treatment efficiency. The method has another problem that it requires an apparatus that can withstand a pressure of 60 atmospheres as in Embodiment 4 and thus the apparatus size increases.

Patent Document 1: Japanese Patent Application Publication No. 2000-24091 (FIG. 1, paragraphs [0009], [0010], and [0040])

Patent Document 2: Japanese Examined Patent Application Publication No. 5-53, (claims 1, 4, 5, for example)

Patent Document 3: Japanese Patent Application Publication No. 2000-157615 (paragraph [0016])

Patent Document 4: Japanese Examined Patent Application Publication No. 7-114674

DISCLOSURE OF THE INVENTION

Problem to be Solved by the Invention

The present invention has an object to provide a method for sterilizing powder or grain by which the heating time is a minimum required time to reduce thermal degradation of the quality of the powder or grain while securing sufficient sterilization effect, and a sterilizing apparatus employing the method. Furthermore, it is another object of the present invention to provide an efficient sterilization method that requires no addition of an antiseptic agent and the like to reduce the cost of powder or grain raw materials. Furthermore, it is another object of the present invention to provide a sterilizing apparatus for killing insects and eggs having a size that is smaller than that of a conventional apparatus by minimizing the required heating time (residence time) of powder or grain to reduce the length of a heated gas flow pipe included in the sterilizing apparatus.

Powder or grain raw materials are used in various industrial fields such as food, dietary supplements, cosmetics, and pharmaceutical products and have various applications. Thus, the contamination of powder or grain raw materials with microorganisms and the like may influence the quality of a final product. In particular, spores living on a powder or grain raw material germinate during distribution process, storage in home, and the like to increase the microbial contamination of the product. To address this, for example, manufacturers set the expiration dates or the freshness dates shorter, use a special distribution method (chilled distribution, frozen distribution, and the like), or add an antiseptic agent, resulting in an increased product cost, inefficient use of the raw material, and compromised safety. On the other hand, the sterilization method by steam heating for easy sterilization has a problem causing quality degradation such as gelatinization of starch, thermal denaturation of protein, decomposition of the molecular structure of a vitamin, and molecular decomposition of pigments such as chlorophyll and polyphenols. Furthermore, as described above, because the sterilization method has a small sterilization effect on heat-resistant bacteria, the treatment temperature and treatment time are required to be increased in order to kill the heat-resistant bacteria completely, and thus the resulting heat history causes unavoidable quality degradation such as the gelatinization of starch.

Means to Solve the Problems

The present invention solves the problems by a method for sterilizing powder or grain, and the method includes applying heat and pressure in which powder or grain is supplied into a heated gas flow pipe kept under heated and pressurized conditions, and the powder or grain is transferred while coming into direct contact with a heated condensable gas in the heated gas flow pipe for 0.008 to 2 seconds, and instantaneous reduced pressure sterilizing in which the heated condensable gas and the powder or grain are instantaneously released into a space having a pressure lower than that in the heated gas flow pipe, water contained in microorganisms adhering to the powder or grain is boiled rapidly, and tissues of the microorganisms are destroyed.

Specifically, first, in the applying of heat and pressure in which the temperature of the microorganisms adhering to the surface of the powder or grain is increased with the powder or grain raw material being transferred while uniformly coming into contact with the heated condensable gas in the heated gas flow pipe, the temperature of the microorganisms themselves such as bacteria and fungi adhering to each surface of the powder or grain is increased. The term "heated condensable gas" here means pressurized steam, saturated steam, and superheated steam. With such condensable gas, the steam is condensed at a saturated steam temperature at a certain pressure, and the latent heat conducts heat to the surface of the microorganisms. Thus, the temperature of the microorganisms present on the surface of the powder or grain can be increased within an extremely short time. For example, by using pressurized steam having a pressure of 0.2 MPaG and a temperature of 133° C., when the powder or grain comes into direct contact with the pressurized steam only for 0.008 to 2 seconds in the applying of heat and pressure, the amount of heat that is large enough to perform the sterilization method of the present invention can be obtained. Considering the quality degradation of the powder or grain, the direct contact time of the pressurized steam and the powder or grain is preferably 0.01 to 2 seconds. The direct contact time is more preferably 0.01 to 1 second and especially preferably 0.01 to 0.5 second. When the direct contact time is such an extremely short time, the temperature of the surface of the powder or grain is increased but that of the inside is increased negligibly. This is because the particle diameter of the powder or grain is far larger than that of the microorganisms. For example, *E. coli* has a diameter of about 0.7 micron and a spore of bacillus as a bacterium has a diameter of about 2 microns. In contrast, as for the powder or grain, for example, powdered tea has a diameter of about 30 microns and wheat flour has a diameter of about 100 microns. In this manner, the applying of heat and pressure has a purpose to provide the condition in which the temperature of the powder or grain itself is increased negligibly to minimize the denaturation of the raw material composition, but only the temperature of the microorganisms on the surface is increased at the saturated steam temperature under a certain pressure.

Subsequent to the applying of heat and pressure, the method proceeds to the instantaneous reduced pressure sterilizing in which the heated condensable gas and the powder or grain are instantaneously released into a space having a pressure lower than that in the heated gas flow pipe. Following the applying of heat and pressure in which the microorganisms adhering to the surface of the powder or grain are heated, the powder or grain exposed to the pressurized condition is instantaneously released under reduced pressure in the step of instantaneous reduced pressure sterilizing, whereby water contained in the microorganisms adhering to the powder or grain is boiled rapidly, and tissues of the microorganisms are destroyed for sterilization. Here, means for instantaneously releasing the heated condensable gas and the powder or grain into a space having a pressure lower than that in the heated gas flow pipe is not specifically limited. A preferred example is a method in which the heated condensable gas and the powder or grain are passed through a pressure reducing unit provided downstream of the heated gas flow pipe to reduce the pressure. Examples of such pressure reducing unit include an orifice and a narrow tube. When the pressure reducing unit such as a narrow tube is used, the mixed gas flow of the powder or grain and the heated condensable gas that is passed through the narrow tube has a high passage speed to lose a large amount of pressure. This results in a differential pressure between the inside of the heated gas flow pipe and the downstream of the narrow tube. By the differential pressure and the minimum thermal energy provided in the applying of heat and pressure, the water contained in the microorganisms is boiled rapidly. In order to properly perform the instantaneous reduced pressure sterilizing of the invention, the passage time through the narrow tube (time for reducing pressure) is preferably, for example, 0.00001 to 0.1 second as a calculated value and the differential pressure is preferably 0.05 to 0.7 MPa. More preferably, the passage time through the narrow tube is 0.00002 to 0.1 second as a calculated value and the differential pressure is 0.05 to 0.5 MPa. Even more preferably, the passage time through the narrow tube is 0.00002 to 0.01 second and the differential pressure is 0.07 to 0.5 MPa.

For example, when the pressure in the heated gas flow pipe is 0.2 MPaG, the temperature of the saturated steam is 133° C., and the residence time in the heated gas flow pipe is about 0.16 second, the temperature inside the spore adhering to the powder or grain is about 133° C. In contrast, in the case of wheat flour, the temperature of the center of the wheat flour is calculated to increase by only several tens of degrees Celsius. Then, the mixed gas flow is passed through the narrow tube within 0.00025 second (calculated value) and released to atmospheric pressure to achieve a reduced pressure by 0.2 MPa instantaneously. Water inside the spores evaporates rapidly because it cannot exist as liquid under atmospheric pressure. As a result, the inside of the spores is filled with a large amount of steam, and the force destroys tissues of the spores to kill the spores.

The narrow tube of the present invention has a certain width in the flow passage direction and differs from the orifice in their shapes. Furthermore, although depending on the shape of the narrow tube or the orifice, in a functional aspect, the powder or grain is difficult to flow through the orifice due to the contracted flow, the orifice thus has a tendency of having a smaller treatment amount but excellent sterilization effect than those of the narrow tube. Conversely, the narrow tube has a tendency of having less sterilization effect but a larger treatment amount than those of the orifice. Therefore, each can be selected depending on the application.

Because only the microorganisms adhering to the surface of the powder or grain are mainly heated but the powder or grain is hardly heated in the applying of heat and pressure, the powder or grain does not swell to burst even through the instantaneous reduced pressure sterilizing. In contrast, the microorganisms instantaneously swell to be killed through the instantaneous reduced pressure sterilizing because they are heated.

As necessary, subsequent to the instantaneous reduced pressure sterilizing, the powder or grain that undergoes instantaneous reduced pressure sterilization in the instantaneous reduced pressure sterilizing may be after-treated by cooling the heated condensable gas and the powder or grain by a non-condensable gas supplied from a cooling unit, and separating the cooled powder or grain from the heated condensable gas and the non-condensable gas. In the cooling, the powder or grain after instantaneous reduced pressure sterilization obtained through the instantaneous reduced pressure sterilizing is mixed with the non-condensable gas supplied from the cooling unit without separating the heated condensable gas and the powder or grain. This step has a purpose to prevent the quality degradation of the powder or grain due to afterheat of the instantaneous reduced pressure sterilizing of the present invention. In the cooling, it is preferable that time from when the powder or grain starts to be transferred by the heated condensable gas until the temperature in a transfer atmosphere of the mixture with the non-condensable gas reaches 65° C. or less is 0.05 to 1 second because the quality degradation of the powder or grain due to the afterheat of the instantaneous reduced pressure sterilizing can be minimized. Even preferably, the time is 0.08 to 1 second.

Means for cooling is not specifically limited but examples thereof include a blower having a high efficiency particulate air filter (HEPA filter) unit, which can filter dust and airborne bacteria to supply a large amount of sterilized non-condensable gas. Furthermore, the "non-condensable gas" here may be any non-condensable gas such as air at room temperature and cooled air as far as the gas can cool the powder or grain by supplying the gas into the sterilizing apparatus for powder or grain. In order to prevent oxidation of the powder or grain by the afterheat and atmospheric oxygen after reduced pressure sterilization, preferably non-condensable gas used is a non-oxidizing gas such as nitrogen gas, argon gas, carbon dioxide gas, and helium gas.

In the separating, the powder or grain cooled in the cooling is separated from the mixed gas of the heated condensable gas and the non-condensable gas. The separation may be performed by any method and, for example, by using a cyclone, a vortex flow is generated in the cyclone container to generate centrifugal force and the powder or grain is separated from the mixed gas by the centrifugal force. When the powder or grain after instantaneous reduced pressure sterilization obtained through the instantaneous reduced pressure sterilizing is immediately separated in the cyclone from the heated condensable gas without undergoing the cooling, the powder or grain whirls to stay in the cyclone to cause the quality degradation of the raw material because the raw material has a temperature of about 100° C. during that time. Furthermore, the powder or grain firstly put into the cyclone does not always come out firstly, and thus the powder or grain having a long residence time has a problem of remarkable quality degradation. Therefore, in the present invention, the powder or grain after instantaneous reduced pressure sterilization is not immediately separated but the mixed gas flow is mixed with the cooled gas to be rapidly cooled within an extremely short time, and thus the temperature is reduced to 65° C. or less in an extremely short time. Then, the powder or grain is separated in the cyclone and the like to solve the problem of quality degradation. A temperature of around 65° C. is the boundary temperature of starch gelatinization or protein denaturation, and thus when the temperature is reduced to 65° C. or less, such denaturation does not develop and oxidation is remarkably delayed.

When the powder or grain is supplied into the heated gas flow pipe, the powder or grain preferably floats in the non-oxidizing gas. This is because if the powder or grain is exposed to a high temperature condition with the presence of oxygen in the heated gas flow pipe, excessive oxidation reaction triggers quality degradation.

By the method for sterilizing powder or grain of the present invention, sterilized powder or grain can be obtained with which quality degradation such as starch gelatinization and protein thermal denaturation by the heat history is minimized. The sterilized powder or grain here means that 1 gram of powder or grain contains 300 (cfu) or less of bacteria.

Furthermore, the method for sterilizing powder or grain and the apparatus employing the method of the present invention have the effect on insect pests and their eggs. The sterilizing method and the apparatus of the present invention have the effect on such insect pests as maize weevil and Indian meal moth and their eggs, and the conditions for killing the insects and eggs are the same as those of the sterilizing method.

As described above, the present invention provides the method in which microorganisms, insect pests, and eggs of insect pests adhering to the surface of powder or grain are heated for a minimum required time, and the powder or grain to which the microorganisms and the like are adhered is rapidly depressurized for instantaneous pressure reduction. The method can be achieved with various apparatuses. A preferred embodiment is a sterilizing apparatus for powder or grain, and the apparatus includes a raw material supplying unit, a heated condensable gas supplying unit, a connector that connects the raw material supplying unit and the heated condensable gas supplying unit, a heated gas flow pipe connected downstream of the connector, a pressure reducing unit provided downstream of the heated gas flow pipe, a cooled gas flow pipe having a midway point to which the pressure reducing unit is connected, a cooling unit that is connected upstream of the cooled gas flow pipe and that feeds a non-condensable gas into the cooled gas flow pipe, and a powder or grain separating apparatus connected downstream of the cooled gas flow pipe.

The configuration of the apparatus will be described later in the detailed description of the present invention given below. By the method for sterilizing powder or grain of the present invention, the time for making the powder or grain in contact with the heated condensable gas can be extremely short. Accordingly, as an apparatus component, the heated gas flow pipe can be a short straight pipe. Specifically, although depending on the inner diameter of the pipe and the flow rate, the heated gas flow pipe having a length of about 100 to 5000 mm can provide sufficient sterilization effect.

Effects of the Invention

By the method for sterilizing powder or grain of the present invention, powder or grain can be sterilized rapidly and simply with minimum quality degradation by a heat history. The present invention has high utility value in the market of powder or grain raw material having serious problems such as thermal denaturation of protein and decomposition of vitamins and pigments. Furthermore, the sterilization method of the present invention kills insect pests and their eggs without compromising the quality of powder or grain.

By performing the cooling in which the powder or grain is cooled immediately after the instantaneous reduced pressure sterilizing, the quality of the powder or grain is not degraded by the residual afterheat during the separating.

By using a non-oxidizing gas when the powder or grain is supplied into the heated gas flow pipe, the powder or grain can be prevented from being oxidized to have degraded quality during the applying of heat and pressure. Similarly, by employing a non-oxidizing gas as the non-condensable gas supplied from the cooling unit, quality degradation by oxidation can be minimized during the cooling and the separating.

By employing the instantaneous reduced pressure sterilizing of the present invention, microorganisms and the like can be killed irrespective of a heat history. This means reduction in the contact time of the powder or grain with the heated condensable gas in the heated gas flow pipe. Thus, the length of the heated gas flow pipe can be made shorter in the apparatus in which the method for killing insects and eggs according to the present invention is performed than in a conventional apparatus. This eliminates the need for a conventional heating cyclone or the like for gaining residence time. Therefore, the apparatus configuration can be further simplified to improve maintainability and to reduce the cost.

EMBODIMENTS FOR CARRYING OUT THE INVENTION

Figure 1:
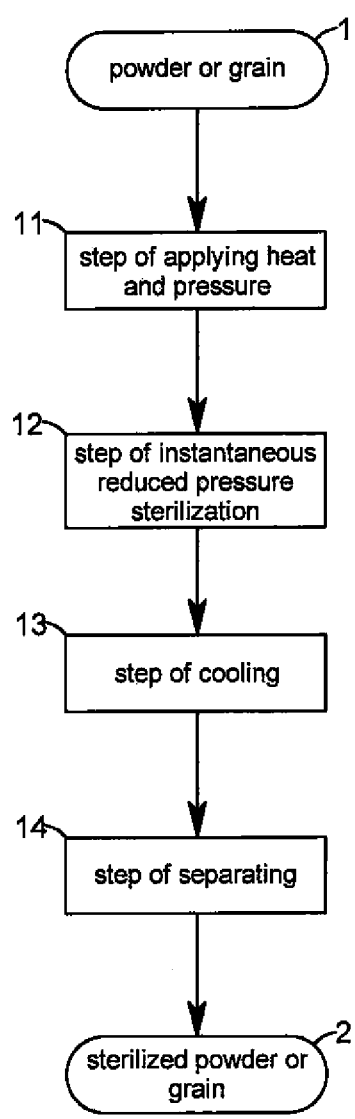
FIG. 1 is a flowchart showing the procedure of a method for sterilizing powder or grain of the present invention.
Figure 2:
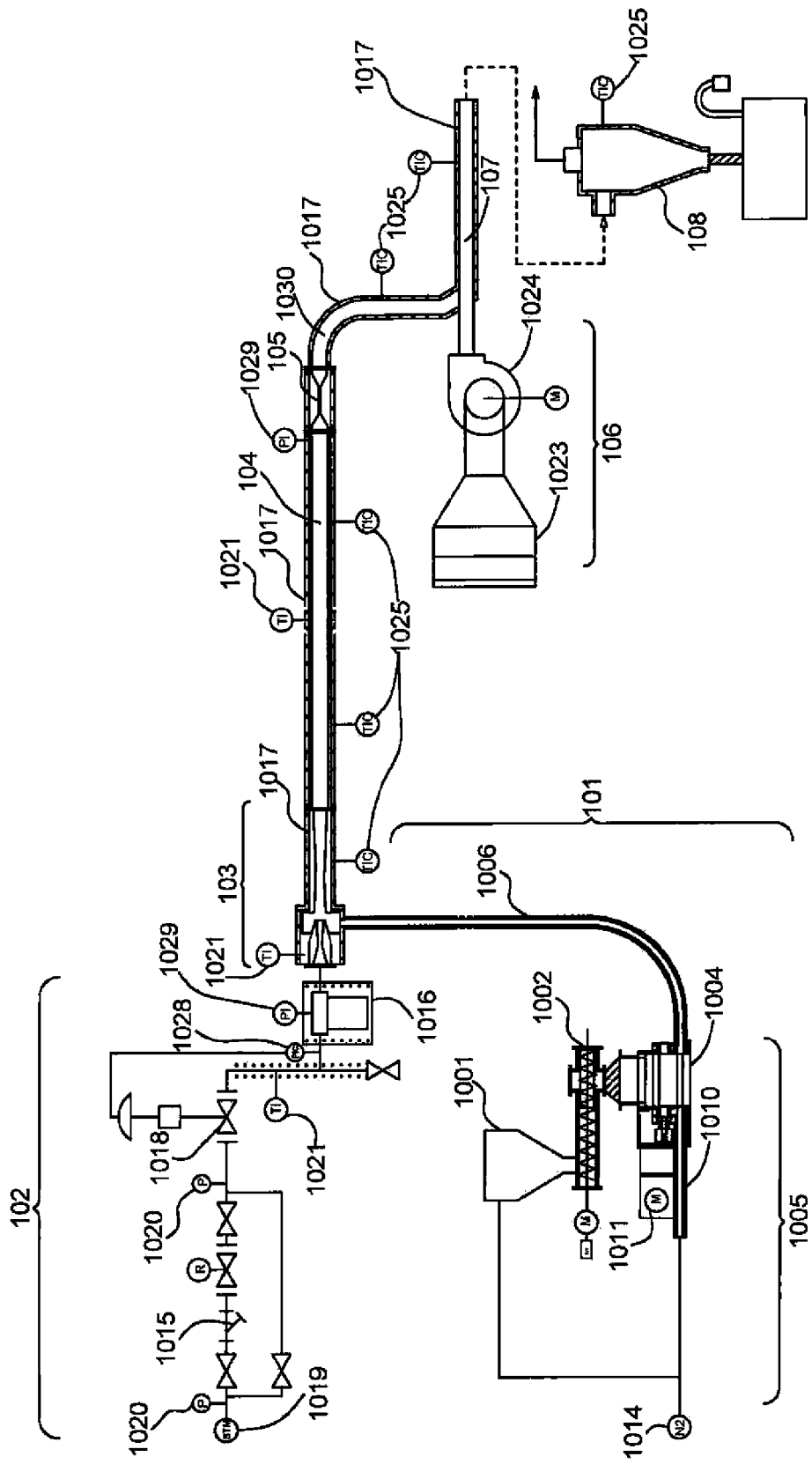
FIG. 2 is a schematic view showing the configuration of an embodiment of a sterilizing apparatus employing the method for sterilizing powder or grain of the present invention.

Hereinafter, an embodiment of the present invention will be specifically described. FIG. 1 is a flowchart showing the procedure of a method for sterilizing powder or grain of the present invention. FIG. 2 is a schematic view showing the configuration of an embodiment of a sterilizing apparatus employing the method for sterilizing powder or grain of the present invention.

As shown in FIG. 1, the present invention provides a step of applying heat and pressure 11 in which powder or grain 1 is supplied into a heated gas flow pipe, and the powder or grain is transferred through the heated gas flow pipe by a heated condensable gas under heated and pressurized conditions, and a step of instantaneous reduced pressure sterilization 12 in which the heated condensable gas and the powder or grain are instantaneously released into a space having a pressure lower than that in the heated gas flow pipe, water contained in microorganisms and the like adhering to the powder or grain is boiled rapidly, and tissues of the microorganisms and the like are destroyed. As necessary, in addition to the two steps, the present invention also provides a step of cooling 13 in which the heated condensable gas and the powder or grain are cooled by a non-condensable gas supplied from a cooling unit, and a step of separating 14 in which the cooled powder or grain is separated from the heated condensable gas and the non-condensable gas. Instantaneous pressure reduction of the present invention is achieved by the step of applying heat and pressure 11 and the step of instantaneous reduced pressure sterilization 12 to obtain sterilized powder or grain 2. However, when the powder or grain is separated from the heated condensable gas, the quality of the powder or grain is degraded by afterheat due to the step of applying heat and pressure 11. Therefore, the step of cooling 13 and the step of separating 14 are preferably performed in combination.

The apparatus shown in FIG. 2 is an embodiment of the sterilizing apparatus suitable for carrying out the method for sterilizing powder or grain of the present invention. In FIG. 2, an ejector 103 is used as a connector connecting a raw material supplying unit 101 and a heated condensable gas supplying unit 102. That is, the sterilizing apparatus for powder or grain includes the raw material supplying unit 101, the heated condensable gas supplying unit 102, the ejector 103 that connects the raw material supplying unit 101 and the heated condensable gas supplying unit 102 and that aspirates the powder or grain with a heated condensable gas, as drive force, supplied from the heated condensable gas supplying unit 102, a heated gas flow pipe 104 connected downstream of the ejector 103, a pressure reducing unit 105 provided downstream of the heated gas flow pipe 104, a cooled gas flow pipe 107 having a midway point to which a pipe 1030 extended from the pressure reducing unit 105 is connected, a cooling unit 106 connected upstream of the cooled gas flow pipe 107, and a powder or grain separating apparatus 108 connected downstream of the cooled gas flow pipe 107.

The raw material supplying unit 101 includes a raw material charging tank 1001, a screw feeder 1002 that is connected downward of the raw material charging tank 1001 and that quantitatively supplies powder or grain filled in the raw material charging tank 1001, a rotary feeder 1004 that is provided downward of the screw feeder 1002 and that supplies the powder or grain quantitatively supplied by the screw feeder 1002 to a raw material supplying pipe 1006, a non-oxidizing gas supplying unit 1014 provided upstream of the rotary feeder 1004, a non-oxidizing gas supplying pipe 1010 connecting the non-oxidizing gas supplying unit 1014 and the rotary feeder 1004, and the raw material supplying pipe 1006 that is connected downstream of the rotary feeder 1004 and through which the powder or grain is aspirated into the ejector 103 with a non-oxidizing gas as a conveying gas supplied from the non-oxidizing gas supplying unit 1014.

In the embodiment, the configuration of the sterilizing apparatus for powder or grain having the non-oxidizing gas supplying unit 1014 has been described, but the non-oxidizing gas supplying unit 1014 is not essential and may be omitted in some cases.

The heated condensable gas supplying unit 102 of the embodiment includes a boiler 1019, a pressure reducing valve unit 1015, a drain separator 1016 separating excess water from steam, a steam control valve 1018, a pressure sensor 1020, and a temperature indicator 1021.

Furthermore, the apparatus according to the embodiment includes a heat insulation jacket 1017. The heat insulation jacket 1017 is provided so as to cover the ejector 103, the heated gas flow pipe 104, the pressure reducing unit 105, the cooled gas flow pipe 107, and the powder or grain separating apparatus 108.

The ejector 103 air-tightly connects the raw material supplying pipe 1006 in the raw material supplying unit 101 with the heated condensable gas supplying unit 102, aspirates the powder or grain in the raw material supplying pipe 1006 with a heated condensable gas as the drive source supplied from the heated condensable gas supplying unit 102, and feeds the powder or grain and the heated condensable gas while stirring them into the heated gas flow pipe 104 provided downstream.

The heated gas flow pipe 104 is air-tightly connected downstream of the ejector 103. For example, by supplying pressurized steam having a pressure of 0.75 MPaG as the drive source to the ejector 103, the ejector 103 aspirates the powder or grain from the raw material supplying pipe 1006 to supply the powder or grain and the pressurized steam into the heated gas flow pipe 104. The pressure in the heated gas flow pipe 104 is kept at the pressure equivalent to the pressure loss occurring while the mixed gas flow of the powder or grain and the pressurized steam is passed through the pressure reducing unit 105. In the case that the pressure is kept at 0.2 MPaG and the temperature is kept at 133° C. in the heated gas flow pipe 104, when the flow rate of the pressurized steam is set at 25 m/second in the heated gas flow pipe 104, a narrow tube is used as the pressure reducing unit 105, and the cross section of the narrow tube is set so that the flow rate of the pressurized steam flowing in the narrow tube will be 300 m/second as a calculated value, a remarkable pressure loss occurs between before and after the narrow tube to achieve instantaneous reduced pressure sterilization. In the embodiment, the heated gas flow pipe 104 has a length of 4000 mm and an inner diameter of 35.7 mm. In this case, the contact time of the pressurized steam and the powder or grain is calculated to be 0.16 second, and microorganisms adhering to the surface of the powder or grain are calculated to be sufficiently heated to 133° C. When the powder or grain has an average particle diameter of several tens of microns or more, the temperature of the center of the powder or grain is calculated to increase by only several tens of degrees Celsius, and thus the powder or grain is calculated to have a minuscule heat history. When the narrow tube has a length of 100 mm, the mixed flow of the pressurized steam and the powder or grain is passed through the narrow tube within 0.00033 second as a calculated value. However, because a differential pressure of 0.2 MPa occurs between before and after the narrow tube, the pressure is instantaneously reduced. At this time, the inside of the bacteria adhering to the surface of the powder or grain is calculated to have a temperature of 133° C. Because the pressure after passing through the narrow tube is almost atmospheric pressure, water in the bacteria is boiled instantaneously to generate a large amount of steam in the bacteria. The force of a large amount of the steam instantaneously generated destroys tissues of the bacteria to kill the bacteria.

The pressure reducing unit 105 is air-tightly connected downstream of the heated gas flow pipe 104. The pressure reducing unit 105 may be any unit capable of achieving a pressure reduction of 0.05 to 0.5 MPa instantaneously (within 0.00001 to 0.1 second). The embodiment uses a narrow tube having an inner diameter of 10.4 mm and a length of 100 mm.

The cooling unit 106 includes a filter unit 1023 having a high-density filter and a blower 1024, and filters dust and airborne bacteria to supply a large amount of sterilized non-condensable gas. As the high-density filter, a high efficiency particulate air filter (HEPA filter) is used. Furthermore, such apparatus components as the filter unit and the blower are not specifically limited as far as the purpose can be achieved. Furthermore, in the embodiment, nitrogen gas is used as the non-condensable gas. The nitrogen gas is supplied from a non-oxidizing gas supplying unit not shown in the schematic.

The cooled gas flow pipe 107 connects the blower 1024 in the cooling unit 106 and the pipe 1030 extended from the pressure reducing unit 105, mixes the powder or grain and the heated condensable gas that are supplied from the pressure reducing unit 105 with the non-condensable gas that is supplied from the cooling unit 106, and feeds the mixture into the powder or grain separating apparatus 108 while cooling the mixture. The cooled gas flow pipe 107 has any length and any inner diameter capable of cooling the powder or grain to a predetermined temperature (in the embodiment, the length is 1000 mm and the inner diameter is 97.6 mm). Furthermore, the cooled gas flow pipe 107 can be simply connected to the cooling unit 106 with a Y-joint. The Y-joint generates a negative pressure near the confluence to aspirate the mixed gas of the heated condensable gas and the powder or grain, and then the non-condensable gas supplied from the cooling unit 106 hits the mixed gas of the heated condensable gas and the powder or grain to efficiently mix the two gas flows having different temperatures from each other.

The powder or grain separating apparatus 108 is connected downstream of the cooled gas flow pipe 107 and separates the powder or grain from the mixed gas of the heated condensable gas and the non-condensable gas. The powder or grain separating apparatus 108 may be any apparatus capable of separating the powder or grain from the mixed gas. The embodiment uses a cyclone.

To evaluate the effects of sterilization, the sterilizing apparatus for powder or grain described above was used as a basic configuration and the apparatus components were properly modified depending on each condition shown in Table 1 to perform sterilization. The quality of powder or grain after sterilization was evaluated by the measurement of gelatinization degree by β-amylase-pullulanase method, the number of bacteria after sterilization (cfu: colony forming unit), and the observation of appearance of the powder or grain. The conditions for sterilization are listed in Table 1. The raw materials in Table mean the raw materials for sterilization. The rice flour+heat-resistant bacteria were obtained by inoculation of $1 \times 10^5$ units of BN strain (*Bacillus subtilis*) purchased from Meiji Seika Kaisha, Ltd. as spores (heat-resistant bacteria) per 1 g of rice flour. The residence time means the time while the powder or grain is in direct contact with the heated condensable gas in the heated gas flow pipe. The treatment time means the time from when the raw material is supplied into the heated gas flow pipe until the raw material is cooled to 65° C. or less and discharged from the cyclone. The starch gelatinization degree of rice flour was 14.1% before sterilization.

TABLE 1

| | | | Driving steam | Inside heated gas flow pipe | | | Pressure | Pressure |
| | Material | Supply (kg/h) | pressure (MPaG) | Pressure (MPaG) | Temperature (° C.) | Residence time (sec) | difference (MPa) | reduction time (sec) |
|---|---|---|---|---|---|---|---|---|
| Example 1 | Rice flour + heat-resistant bacteria | 50 | 0.75 | 0.2 | 133 | 0.01 | 0.2 | 0.00033 |
| Example 2 | Rice flour + heat-resistant bacteria | 50 | 0.75 | 0.2 | 133 | 0.16 | 0.2 | 0.00033 |
| Comp. Example 1 | Rice flour + heat-resistant bacteria | 50 | 0.75 | 0.2 | 133 | 0.005 | 0.2 | 0.00033 |
| Comp. Example 2 | Rice flour + heat-resistant bacteria | 15 | 0.75 | 0.2 | 133 | 0.16 | 0.2 | 0.000005 |

TABLE 1-continued

| | | | | | | | | |
|---|---|---|---|---|---|---|---|---|
| Example 3 | Rice flour + heat-resistant bacteria | 50 | 0.75 | 0.2 | 133 | 2.0 | 0.2 | 0.00033 |
| Comp. Example 3 | Rice flour + heat-resistant bacteria | 50 | 0.75 | 0.2 | 133 | 2.5 | 0.2 | 0.00033 |
| Example 4 | Rice flour + heat-resistant bacteria | 50 | 0.75 | 0.2 | 133 | 0.16 | 0.2 | 0.1 |
| Comp. Example 4 | Rice flour + heat-resistant bacteria | 50 | 0.75 | 0.2 | 133 | 0.16 | 0.2 | 0.2 |
| Example 5 | Rice flour + heat-resistant bacteria | 50 | 0.75 | 0.05 | 111 | 0.16 | 0.05 | 0.00033 |
| Comp. Example 5 | Rice flour + heat-resistant bacteria | 50 | 0.75 | 0.03 | 107 | 0.16 | 0.03 | 0.00033 |
| Example 6 | Rice flour + heat-resistant bacteria | 50 | 1.0 | 0.5 | 158 | 0.16 | 0.5 | 0.00033 |
| Example 7 | Rice flour + heat-resistant bacteria | 50 | 1.0 | 0.6 | 164 | 0.16 | 0.6 | 0.00033 |
| Example 8 | Rice flour + heat-resistant bacteria | 50 | 0.75 | 0.2 | 133 | 1.0 | 0.2 | 0.00033 |
| Example 9 | Rice flour + heat-resistant bacteria | 50 | 0.75 | 0.2 | 133 | 0.48 | 0.2 | 0.00033 |
| Example 10 | Rice flour + heat-resistant bacteria | 50 | 0.75 | 0.2 | 133 | 0.008 | 0.2 | 0.00033 |

| | Treatment time (sec) | Bacteria count before treatment (cfu) | Bacteria count after treatment (cfu) | Notes |
|---|---|---|---|---|
| Example 1 | 0.6 | $1 \times 10^5$ | <300 | Narrow tube used for pressure reduction. Gelatinization degree: 14.2% |
| Example 2 | 0.8 | $1 \times 10^5$ | <300 | Narrow tube used for pressure reduction. Gelatinization degree: 14.5% |
| Comparative Example 1 | 0.6 | $1 \times 10^5$ | $2 \times 10^3$ | Narrow tube used for pressure reduction. |
| Comparative Example 2 | 0.8 | $1 \times 10^5$ | <300 | Orifice used for pressure reduction, whose small inner diameter caused a contracted flow and an extremely small throughout. |
| Example 3 | 2.6 | $1 \times 10^5$ | <300 | Narrow tube used for pressure reduction. Gelatinization degree: 16.0% |
| Comparative Example 3 | 3.1 | $1 \times 10^5$ | <300 | Narrow tube used for pressure reduction. Gelatinization degree: 21.0% |
| Example 4 | 0.9 | $1 \times 10^5$ | <300 | Narrow tube used for pressure reduction. |
| Comparative Example 4 | 1.0 | $1 \times 10^5$ | $3 \times 10^3$ | Rotary valve used for pressure reduction. |
| Example 5 | 0.8 | $1 \times 10^5$ | <300 | Narrow tube used for pressure reduction. |
| Comparative Example 5 | 0.8 | $1 \times 10^5$ | $1 \times 10^3$ | Narrow tube used for pressure reduction. |
| Example 6 | 0.8 | $1 \times 10^5$ | <300 | Narrow tube used for pressure reduction. Rice flour swelled slightly. |
| Example 7 | 0.8 | $1 \times 10^5$ | <300 | Narrow tube used for pressure reduction. Some rice flour swelled to burst within an acceptable range depending on applications. |
| Example 8 | 1.6 | $1 \times 10^5$ | <300 | Narrow tube used for pressure reduction. Gelatinization degree: 15.2% |
| Example 9 | 1.08 | $1 \times 10^5$ | <300 | Narrow tube used for pressure reduction. Gelatinization degree: 14.9% |
| Example 10 | 0.608 | $1 \times 10^5$ | <500 | Narrow tube used for pressure reduction. Gelatinization degree: 14.2% |

As shown in Example 1 and Example 2 in Table 1, when the temperature in the heated gas flow pipe was 133° C. and the residence time was 0.01 to 0.16 second, the number of bacteria became 300 cfu or less and the starch gelatinization degree was 14.2 to 14.5% after the treatment. The starch gelatinization degree was almost the same as that of 14.1% before the treatment. Thus, according to the invention, sufficient sterilization effect can be obtained on the heat-resistant bacterium with the quality of the powder or grain being kept. Alternatively, as in Examples 8 and 9, when the residence time was 1.0 second or 0.48 second, each starch gelatinization degree was a little higher but within an acceptable range depending on applications. As in Example 10, when the residence time in the heated gas flow pipe was 0.008 second, the sterilization effect was reduced a little but still observed.

In contrast, as in Comparative Example I, when the residence time was shortened (0.005 second), sufficient sterilization effect was not obtained ($2 \times 10^3$ cfu). As in Comparative Example 2, when an orifice was used as the pressure reducing unit and the pressure reduction time was shortened (0.000005 second), sufficient sterilization effect was obtained (300 cfu or less) but the orifice caused a contracted flow and it was thus difficult for the powder or grain to pass therethrough (the orifice had an inner diameter of 9 mm). Thus, the throughput of powder or grain was reduced (15 kg/h) in comparison with the throughput in other sterilization conditions, and it is therefore unsuitable for practical use.

As in Example 3, even when the residence time in the heated gas flow pipe was slightly longer (2 seconds), the starch gelatinization degree did not increase to a large extent (16.0%), and sufficient sterilization effect (300 cfu or less) was obtained on the heat-resistant bacterium. In contrast, as in Comparative Example 3, when the residence time was over 2 seconds (2.5 seconds), sufficient sterilization effect was obtained on the heat-resistant bacterium but the starch gelatinization increased (21.0%) unfavorably.

As for the pressure reduction time, as shown in Comparative Example 4, when a rotary valve was employed as the pressure reducing unit, some time was required to reach the reduced pressure (0.2 second) and sufficient sterilization effect was not obtained ($3 \times 10^3$). In contrast, as in Example 4, when a narrow tube was used as the pressure reducing unit to reduce pressure, the reduced pressure was rapidly achieved (a pressure reduction time of 0.1 second), and sufficient sterilization effect was obtained on the heat-resistant bacterium (300 cfu or less).

As for the differential pressure generated by the pressure reducing unit, as in Example 5, when the pressure in the heated gas flow pipe was 0.05 MPaG and heating was performed with the pressurized steam, the temperature in the heated gas flow pipe increased to 111° C. and the differential pressure generated by the pressure reducing unit reached 0.05 MPa. It was revealed that sufficient sterilization effect was obtained on the heat-resistant bacterium in this condition (300 cfu or less). In contrast, as shown in Comparative Example 5, when the pressure in the heated gas flow pipe was 0.03 MPaG and heating was performed with the pressurized steam, the temperature in the heated gas flow pipe increased to 107° C. and the differential pressure generated by the pressure reducing unit reached 0.03 MPa. Under this differential pressure, sufficient sterilization effect was not obtained on the heat-resistant bacterium (1×10³ cfu).

As shown in Example 6, when the pressure in the heated gas flow pipe was 0.5 MPa and heating was performed with the pressurized steam, the temperature in the heated gas flow pipe increased to 158° C. and the differential pressure generated by the pressure reducing unit reached 0.5 MPa. In this condition, the sterilization effect was satisfactory on the heat-resistant bacterium (300 cfu or less) but the rice flour swelled slightly. In contrast, as in Example 7, when the pressure in the heated gas flow pipe was 0.6 MPa and heating was performed with the pressurized steam, the temperature in the heated gas flow pipe increased to 164° C. and the differential pressure generated by the pressure reducing unit reached 0.6 MPa. In this condition, the sterilization effect was also satisfactory on the heat-resistant bacterium (300 cfu or less) and some of the rice flour swelled to burst. However, the burst reduced the particle diameter of the powder or grain to be preferred depending on applications.

Rice bran was sterilized with the sterilizing apparatus for powder or grain of the present invention, and the number of bacteria (cfu: colony forming unit) was counted before and after sterilization. The measurement results are listed in Table 2. Example 11 in Table 2 reveals that the present invention is effective on the sterilization of rice bran and has sufficient sterilizability with respect to viable bacteria adhering to rice bran.

TABLE 2

| | Material | Supply (kg/h) | Driving steam pressure (MPaG) | Inside heated gas flow pipe Pressure (MPaG) | Temperature (° C.) | Residence time (sec) | Pressure difference (MPa) | Pressure reduction time (sec) | Treatment time (sec) | Bacteria count before treatment (cfu) | Bacteria count after treatment (cfu) | Notes |
|---|---|---|---|---|---|---|---|---|---|---|---|---|
| Example 11 | Rice bran | 50 | 0.75 | 0.2 | 133 | 0.16 | 0.2 | 0.00033 | 0.8 | $2.7 \times 10^5$ | <300 | Narrow tube used for pressure reduction. |

Next, green tea powder was sterilized with the sterilizing apparatus for powder or grain of the present invention, and the number of bacteria (cfu: colony forming unit) was counted before and after sterilization, and the quality after sterilization was evaluated by a sensory test. The sterilization conditions and the test results are listed in Table 3. In the sterilization, the residence time in the heated gas flow pipe was controlled so that the powder or grain would have a temperature of 64° C. when discharged from the cyclone.

TABLE 3

| | Material | Supply (kg/h) | Driving steam pressure (MPaG) | Inside heated gas flow pipe Pressure (MPaG) | Temperature (° C.) | Residence time (sec) | Pressure difference (MPa) | Pressure reduction time (sec) | Treatment time (sec) |
|---|---|---|---|---|---|---|---|---|---|
| Comp. Example 6 | Tea powder | 50 | 0.75 | 0.2 | 133 | 0.01 | 0.2 | 0.00033 | 0.03 |
| Example 12 | Tea powder | 50 | 0.75 | 0.2 | 133 | 0.01 | 0.2 | 0.00033 | 0.05 |
| Example 13 | Tea powder | 50 | 0.75 | 0.2 | 133 | 0.9 | 0.2 | 0.00033 | 1.0 |
| Comp. Example 7 | Tea powder | 50 | 0.75 | 0.2 | 133 | 1.4 | 0.2 | 0.00033 | 1.5 |

| | Bacteria count before treatment (cfu) | Bacteria count after treatment (cfu) | Temperature after discharged from cyclone | Evaluation | Notes |
|---|---|---|---|---|---|
| Comp. Example 6 | $3 \times 10^3$ | <300 | 72 | Not reduced to 65 C.° or less. | Narrow tube used for pressure reduction. |

TABLE 3-continued

| | | | | | |
|---|---|---|---|---|---|
| Example 12 | $3 \times 10^3$ | <300 | 64 | Flavor and color not changed. | Narrow tube used for pressure reduction. |
| Example 13 | $3 \times 10^3$ | <300 | 64 | Flavor and color slightly changed. No merchantability problem. | Narrow tube used for pressure reduction. |
| Comp. Example 7 | $3 \times 10^3$ | <300 | 64 | Flavor changed. Slightly lighter color. Certain merchantability problem. | Narrow tube used for pressure reduction. |

As shown in Example 12, when the treatment time was 0.05 second for sterilization, the powder or grain was cooled to 64° C. when discharged from the cyclone. The powder or grain after sterilization kept the original flavor and color shade, which means the quality did not degrade. In addition, sufficient sterilization effect was obtained (300 cfu or less). In contrast, as in Comparative Example 6, when the treatment time (the time from when the raw material was supplied into the heated gas flow pipe until it was discharged from the cyclone) was 0.03 second, the cooling time was insufficient and thus the temperature of the powder or grain was not reduced to 65° C. or less when discharged from the cyclone.

When the treatment time was 1 second in the condition shown in Example 13, the residence time in the heated gas flow pipe was 0.9 second and sufficient sterilization effect was obtained (300 cfu or less) but the flavor and color shade changed a little. However, the quality of commodities was not affected. In contrast, when the treatment time was 1.5 seconds in the condition shown in Comparative Example 7 for the treatment, the residence time in the heated gas flow pipe was 1.4 seconds and sufficient sterilization effect was obtained (300 cfu or less). However, the green tea powder after sterilization was changed, for example, in flavor or to have slightly lighter color, and thus the quality of commodities was affected.

In this manner, according to the present invention, various powder or grain raw materials can be sterilized without quality degradation due to heating. Furthermore, according to the present invention, heat-resistant bacteria that have been difficult to kill can be killed continuously, and therefore the industrial utility value is extremely high.

Next, the rice flour that was left until Indian meal moth or maize weevil infests was treated in the same respective conditions as those in Examples 1 to 10 and Comparative Examples 1 to 5 in Table 1. The rice flour immediately after the treatment was observed whether Indian meal moth or maize weevil lived or not. Then, the treated rice flour was put into a Petri dish, the dish was sealed with surgical tape and put into an incubator at 30° C. for a week, and then egg eclosion was checked. The results are listed in Table 4.

TABLE 4

| | Material | Conditions same as | Insect pest | Survival | Eclosion | Notes |
|---|---|---|---|---|---|---|
| Example 14 | Rice flour | Example 1 | Indian meal moth | None | None | Narrow tube used for pressure reduction. Gelatinization degree: 14.2% |
| Example 15 | Rice flour | Example. 2 | Indian meal moth | None | None | Narrow tube used for pressure reduction. Gelatinization degree: 14.5% |
| Comp. Example 9 | Rice flour | Comp. Example 1 | Indian meal moth | Observed | Observed | Narrow tube used for pressure reduction. |
| Comp. Example 10 | Rice flour | Comp. Example 2 | Indian meal moth | None | None | Orifice used for pressure reduction, whose small inner diameter caused a contracted flow and an extremely small throughput. |
| Example 16 | Rice flour | Example 3 | Indian meal moth | None | None | Narrow tube used for pressure reduction. Gelatinization degree: 16.0% |
| Comp. Example 11 | Rice flour | Comp. Example 3 | Indian meal moth | None | None | Narrow tube used for pressure reduction. Gelatinization degree: 21.0% |
| Example 17 | Rice flour | Example 4 | Indian meal moth | None | None | Narrow tube used for pressure reduction. |
| Comp. Example 12 | Rice flour | Comp. Example 4 | Indian meal moth | Observed | Observed | Rotary valve used for pressure reduction. |
| Example 18 | Rice flour | Example 5 | Maize weevil | None | None | Narrow tube used for pressure reduction. |
| Comp. Example 13 | Rice flour | Comp. Example 5 | Maize weevil | Observed | Observed | Narrow tube used for pressure reduction. |
| Example 19 | Rice flour | Example 6 | Maize weevil | None | None | Narrow tube used for pressure reduction. Rice flour swelled slightly. |
| Example 20 | Rice flour | Example 7 | Maize weevil | None | None | Narrow tube used for pressure reduction. Some rice flour swelled to burst. |
| Example 21 | Rice flour | Example 8 | Maize weevil | None | None | Narrow tube used for pressure reduction. Gelatinization degree: 15.2% |
| Example 22 | Rice flour | Example 9 | Maize weevil | None | None | Narrow tube used for pressure reduction. Gelatinization degree: 14.9% |
| Example 23 | Rice flour | Example 10 | Maize weevil | None | None | Narrow tube used for pressure reduction. Gelatinization degree: 14.2% |

Table 4 reveals that Indian meal moth, maize weevil, and their eggs having infested the rice flour are killed in a reliable manner according, to the present invention. In addition to Indian meal moth and maize weevil, the method for killing insects and eggs of the present invention has the effect on flour beetle adhered to wheat flour.

| Reference Numerals | |
|---|---|
| 1 | powder or grain |
| 2 | sterilized powder or grain |
| 11 | step of applying heat and pressure |
| 12 | step of instantaneous reduced pressure sterilization |
| 13 | step of cooling |
| 14 | step of separating |
| 101 | raw material supplying unit |
| 102 | heated condensable gas supplying unit |
| 103 | ejector |
| 104 | heated gas flow pipe |
| 105 | pressure reducing unit |
| 106 | cooling unit |
| 107 | cooled gas flow pipe |
| 108 | powder or grain separating apparatus |
| 1001 | raw material charging tank |
| 1002 | screw feeder |
| 1004 | rotary feeder |
| 1006 | raw material supplying pipe |
| 1007 | rotor |
| 1008 | hopper |
| 1009 | rotor groove |
| 1010 | non-oxidizing gas supplying pipe |
| 1011 | motor |
| 1014 | non-oxidizing gas supplying unit |
| 1015 | pressure reducing valve unit |
| 1016 | drain separator |
| 1017 | heat insulation jacket |
| 1018 | steam control valve |
| 1019 | boiler |
| 1020 | pressure sensor |
| 1021 | temperature indicator |
| 1023 | filter unit |
| 1024 | blower |
| 1025 | temperature control sensor |
| 1026 | rotor rotary shaft |
| 1027 | Y-joint |
| 1028 | pressure control sensor |
| 1029 | pressure indicator |
| 1030 | pipe |
| 1031 | inlet of heated condensable gas and powder or grain |
| 1032 | inlet of non-condensable gas |
| 1033 | outlet |

The invention claimed is:

1. A method for sterilizing powder or grain, comprising:
applying heat and pressure in which powder or grain is supplied into a heated gas flow pipe kept under heated and pressurized conditions, and the powder or grain is transferred while coming into direct contact with a heated condensable gas in the heated gas flow pipe for 0.008 to 2 seconds;
sterilizing with instantaneous reduced pressure the powder or grain, wherein the heated condensable gas and the powder or grain are instantaneously released into a space having a pressure lower than that in the heated gas flow pipe, water contained in microorganisms adhering to the powder or grain is boiled rapidly, and tissues of the microorganisms are destroyed,
cooling the heated condensable gas and the powder or grain by a non-condensable gas supplied from a cooling unit; and
separating the cooled powder or grain from the heated condensable gas and the non-condensable gas,
wherein in the step of sterilizing, the heated condensable gas and the powder or grain is passed through a pressure reducing unit provided downstream of the heated gas flow pipe to perform a pressure reduction process, and the pressure reduction process is achieved within 0.00001 to 0.1 second.

2. The method for sterilizing powder or grain according to claim 1, wherein in the step of sterilizing with instantaneous reduced pressure, the heated condensable gas and the powder or grain are released in the space having a pressure that is 0.05 to 0.7 MPa lower than a pressure in the step of applying heat and pressure.

3. The method for sterilizing powder or grain according to claim 1, wherein
in the step of cooling, the heated condensable gas and the powder or grain are mixed with the non-condensable gas supplied from the cooling unit without separating the heated condensable gas and the powder or grain, and
time from when the powder or grain starts to be transferred by the heated condensable gas until the temperature in a transfer atmosphere of the mixture with the non-condensable gas reaches 65° C. or less is 0.05 to 1 second.

4. The method for sterilizing powder or grain according to claim 1, wherein the powder or grain is supplied into the heated gas flow pipe by a non-oxidizing gas.

* * * * *